United States Patent [19]
Ferguson et al.

[11] Patent Number: 6,042,557
[45] Date of Patent: Mar. 28, 2000

[54] ORTHOPEDIC SPLINTS AND METHODS OF MAKING SAME

[75] Inventors: Ken R. Ferguson, Charlotte; James V. Snipes, Winston-Salem, both of N.C.

[73] Assignee: K.R. Ferguson Technologies, Inc., Charlotte, N.C.

[21] Appl. No.: 09/095,452

[22] Filed: Jun. 10, 1998

[51] Int. Cl.[7] ............................................... A61F 5/00
[52] U.S. Cl. ........................................ 602/6; 602/5; 602/8
[58] Field of Search .............................. 602/6, 5, 41, 46, 602/1, 8

[56] References Cited

U.S. PATENT DOCUMENTS

| | | |
|---|---|---|
| 3,900,024 | 8/1975 | Lauber et al. . |
| 4,683,877 | 8/1987 | Ersfeld et al. . |
| 4,770,299 | 9/1988 | Parker . |
| 4,946,726 | 8/1990 | Sandvig et al. . |
| 5,334,442 | 8/1994 | Okamoto et al. . |
| 5,409,448 | 4/1995 | Kelley . |
| 5,415,622 | 5/1995 | Kelley . |
| 5,454,780 | 10/1995 | Duback et al. . |
| 5,544,663 | 8/1996 | Duback . |
| 5,718,674 | 2/1998 | Penrose ................................. 602/46 |
| 5,720,714 | 2/1998 | Penrose ................................. 602/6 |

FOREIGN PATENT DOCUMENTS 326 285 B1  8/1993  European Pat. Off. .

*Primary Examiner*—John G. Weiss
*Assistant Examiner*—Kelvin Hart
*Attorney, Agent, or Firm*—Alston & Bird LLP

[57] ABSTRACT

Articles and methods for forming splints for body parts of an animal are disclosed. A splint includes a splint core formed of one or more layers of knit fabric impregnated with a water-curable hardenable resin. The opposite faces of the splint core are covered by nonwoven fibrous fabric covers which bond to the core by contact with the resin. A securement member or strap is partially or completely encircled about the splint, and flexible hooks on the strap grasp the fabric covers to hold the splint on the body part being treated. For a small animal, the splint core is a die-cut article having notches in its side edges which permit the core to be bent to form a foot-supporting platform without substantial bunching at the side edges.

35 Claims, 4 Drawing Sheets

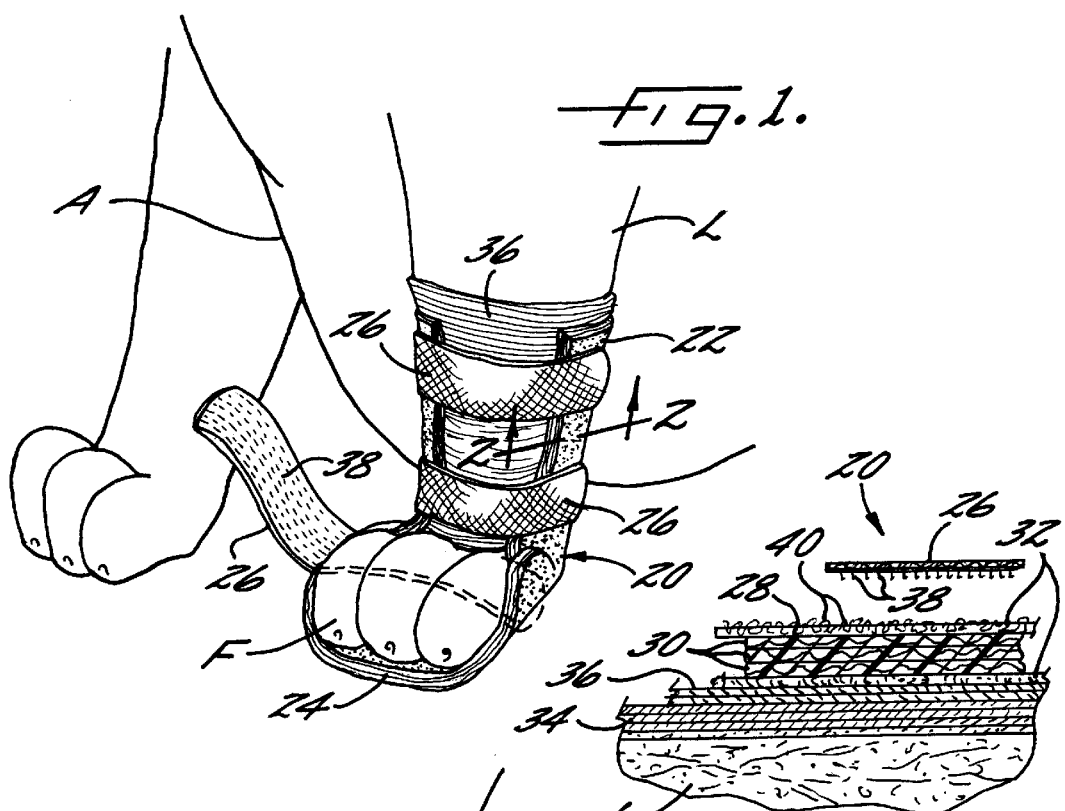
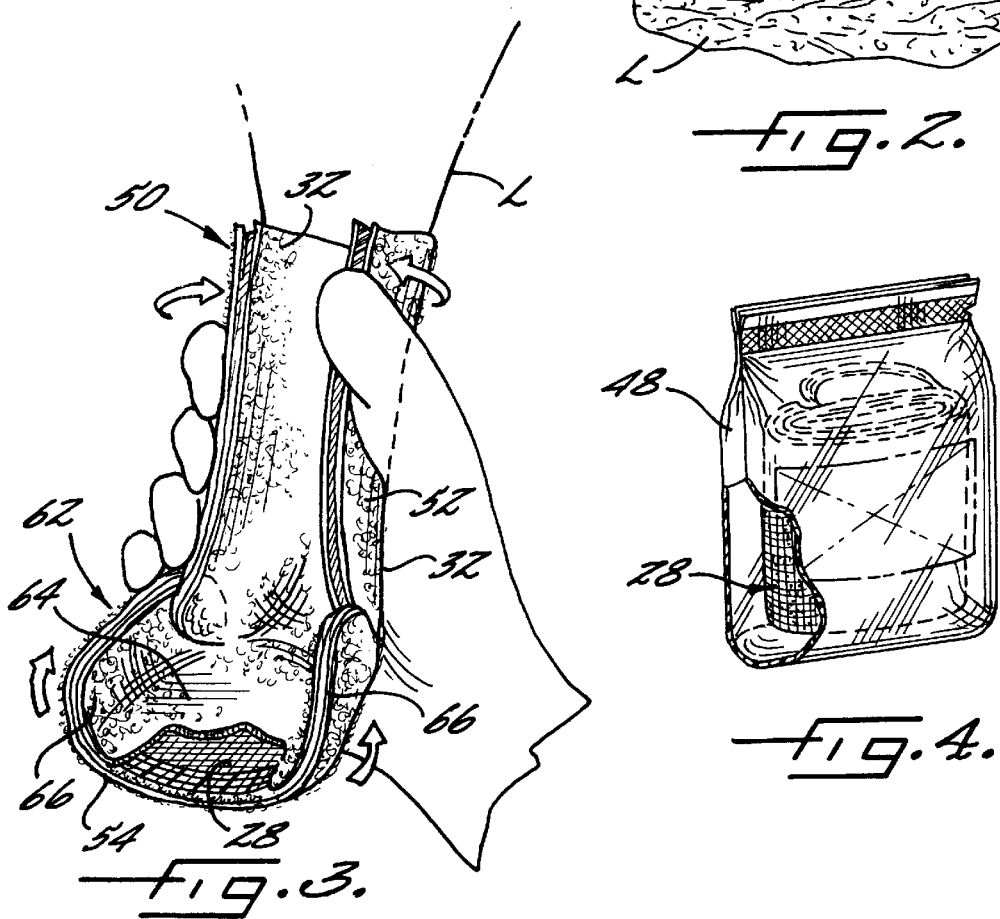

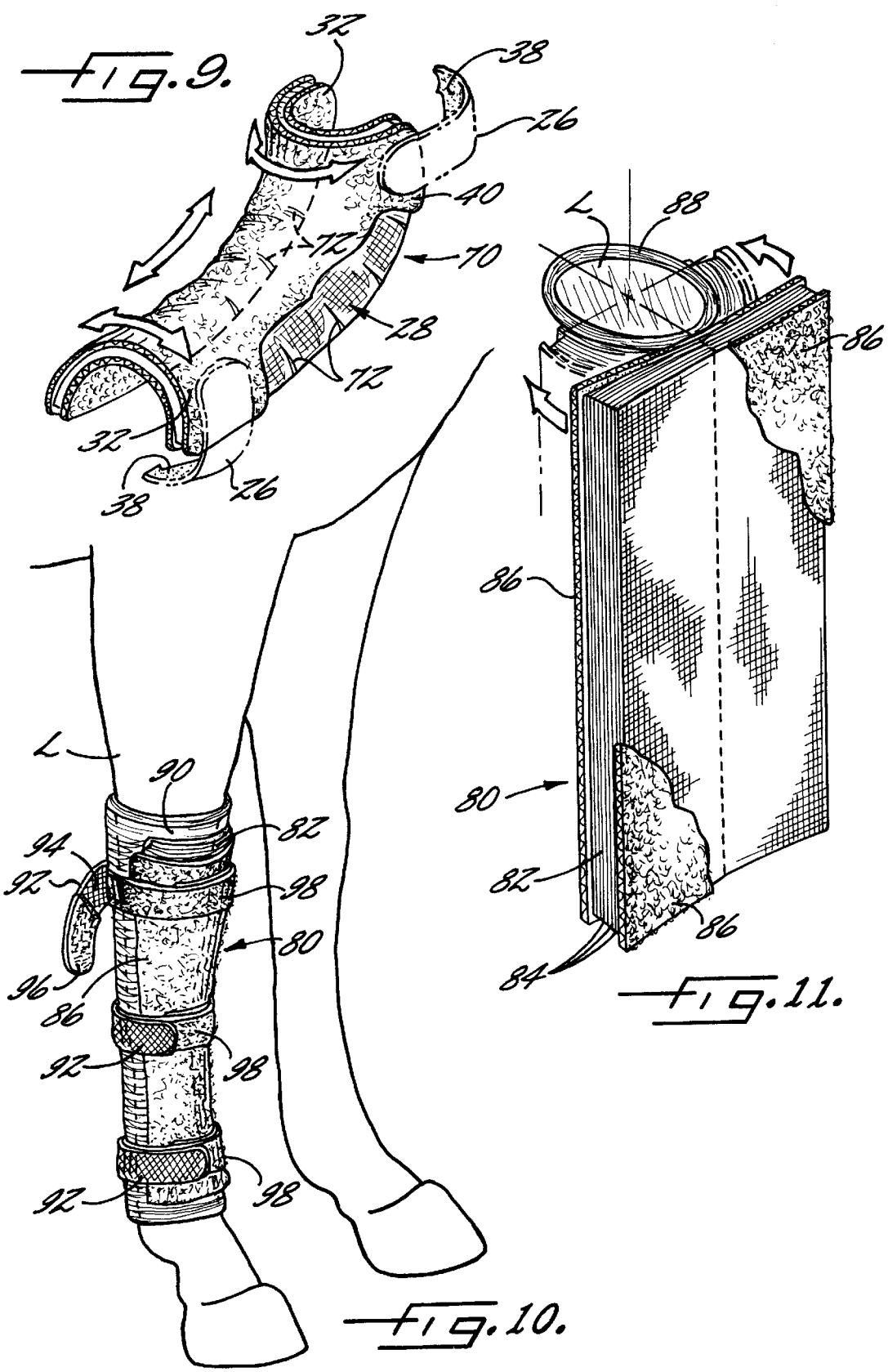

ORTHOPEDIC SPLINTS AND METHODS OF MAKING SAME

FIELD OF THE INVENTION

The present invention relates to orthopedic splints and methods of making such splints. More particularly, the invention relates to orthopedic splints of the type which are applied to a limb or other body part in a flexible state and then allowed to harden to form a custom-shaped splint.

BACKGROUND OF THE INVENTION

Orthopedic casts and splints are frequently used in the treatment of both humans and other animals where it is necessary to inhibit motion of a limb which has sustained a fracture, for example to prevent bending of the limb at a joint. They are also used, particularly in the veterinary field, to protect wounds even in the absence of a fracture, to allow them to heal without being subjected to additional trauma which can hinder the healing process. The term cast is used herein to refer generally to a rigid article which completely encircles a limb or other body part. Thus, casts typically cannot be removed without cutting or otherwise destroying the integrity of the cast. In contrast, the term splint is used to refer to a rigid article which can be removed from the body part in one piece.

In the veterinary field, splints tend to be preferred over casts for treating fractures because the great majority of the cases of limb fractures are caused by blunt force trauma, and accordingly there typically is a tissue wound associated with the fracture which must periodically be attended to during the treatment period. Thus, splints offer the advantage of being removable and replaceable to allow the practitioner to treat the wound and re-splint the limb.

In the treatment of humans, use of custom-shaped splints has increased because of the ability of the splints to properly fit the body part being treated so as to avoid pressure points against the body part. Such pressure points can cause a variety of problems, including pressure ulcers and the like. Patients tend to prefer custom-shaped splints also, because of the improved comfort they provide.

Various types of articles for forming custom-shaped casts, splints, or other body part protectors, have been developed for use by humans. Most of the currently available articles utilize a flexible strip or sheet of foam or fabric which is impregnated with a water-curable resin which cures and hardens within a relatively short time after being exposed to water. The strip or sheet in some cases includes a protective and cushioning cover such as foam or fabric. The strip or sheet is soaked in water, and is then wrapped or otherwise applied to the body part being splinted. The cast or splint is allowed to cure while applied to the body part, and the result is a rigid splint which substantially conforms to the shape of the body part.

Prior to the present invention, however, most of the splinting and casting articles and methods have been oriented toward splinting materials which are limited in the extent to which they can be modified in size for properly fitting a body part to be splinted. Furthermore, most of the splinting methods have not been well suited to emergency use in the field, where materials and time may be limited.

For instance, U.S. Pat. No. 5,334,442 discloses an orthopedic sheet-like composition for forming a cast or splint which comprises an inner pliant sheet impregnated with a water-curable resin, and a pair of composite fabric portions contacting at least one side and covering both sides of the pliant sheet. The composite fabric portions comprise triple-layered knit fabric. In one disclosed embodiment, a layer of closed-cell foam is adhered between one of the composite fabric portions and the pliant impregnated sheet, and a double-sided adhesive tape is applied between a peripheral area of the other fabric portion and the pliant impregnated sheet, so as to prevent dislodgement of the pliant sheet, the fabrics, and the closed-cell foam material. The sheet-like composition is stored and sealed within a package filled with inert gas. Just prior to use, the package is opened and the composition is removed, and the composition is dipped in water briefly and then removed from the water and shaken to remove excess water. The composition is then applied to the body part and deformed by hand to conform to the body part. It will be appreciated that a pre-fabricated structure having a fixed length and width such as that disclosed in the '442 patent may not be suitable for making a custom-fitted splint in the field. For instance, where the width of the structure exceeds about half the circumference of the body part to be splinted, a splint made from the structure will wrap more than halfway around the body part and hence will not be removable to permit inspection of and treatment of the injury site. Because the composition disclosed by the '442 patent comprises a unitary structure held together at its periphery, it is limited in the extent to which it can be modified by the practitioner in the field to adapt the size, and particularly the width, of the composition, to the particular body part to be treated.

U.S. Pat. No. 3,900,024 discloses an orthopedic cast and method of making the same, in which a first sheet of deformable water absorptive resilient material, preferably foam rubber or urethane foam, is placed on a working surface and trimmed to the appropriate size, and a number of sheets of gauze impregnated with dry plaster are individually placed over the first sheet in general alignment therewith. A second sheet of the water absorptive deformable material is trimmed to the appropriate size and placed over the plaster sheets. The two outer sheets are sized so that the peripheral edges of the sheets extend somewhat beyond the edges of the plaster sheets. These peripheral edges of the outer sheets are joined together such as by adhesive so as to form a sandwich construction or blank. The blank is saturated with water and excess water drained and pressed from the blank, and the blank is then applied to the body part. The necessity of preparing and individually placing a number of plaster-impregnated gauze sheets on the lower foam sheet, and then adhesively joining the upper and lower foam sheets together along their edges, makes the method of the '024 patent time consuming. Additionally, a practitioner in the field may not always have adhesive available. Accordingly, the method is not well suited for emergency use in the field where time and availability of materials may be limited.

U.S. Pat. No. 5,454,780 discloses a custom body protective device, such as a shin guard or the like, which comprises an initially flexible intermediate layer of fiberglass fabric impregnated with water-curable resin, and a pair of outer cushion layers of foam material laminated to a heavy knitted coating. The edges of the outer cushion layers are stitched together to enclose the resin-impregnated intermediate layer, forming a pre-fabricated product. The device is exposed to water and applied to a body part and is allowed to cure to form a protector for the body part. The protector may be secured to the body part by a strap having hook and loop fastener members. U.S. Pat. No. 5,544,663 discloses a protector similar to that of the '780 patent, and further discloses that patches of non-woven loop material can be sewn onto the outer surfaces of the cushion layers for cooperating with patches of hook material attached to opposite ends of an elastic strap to hold the protector on a leg. The pre-fabricated protectors of the '780 and '663 patents are not readily modifiable in size and shape, since trimming off a portion of the protector would remove the edge stitching and thus destroy the desired integrity of the structure.

Another problem associated with veterinary uses of splints is that many types of animals will chew at or try to remove a splint that causes discomfort to the animal because of poor fit, and in the process the animal may do additional damage to the area of treatment. Further, if the animal succeeds in removing the splint, additional injury and/or impairment of the healing process may likely occur. Pre-fabricated splints frequently do not fit properly, and therefore have the potential to cause discomfort and the aforementioned problems attendant thereto.

Furthermore, because animals may attempt to remove a splint, the fastening of the splint to the animal's body part must be such as to resist the animal's attempt to remove it. Fastening systems which may be suitable for use by humans, such as an ordinary bandaging material wrapped around the splint to hold it in place, are typically not well suited to use on animals. Additionally, and as previously noted, since a veterinary practitioner may wish to periodically remove a splint to treat an associated wound and then replace the splint, the fastening system should be convenient in its use. Thus, there is a need for splints and splinting articles for custom-shaping of splints having adequate fastening systems for use in the veterinary field.

SUMMARY OF THE INVENTION

The present invention in one preferred embodiment provides a splint having a fastening system which facilitates secure fastening of the splint to a body part as well as convenient removal and replacement of the splint.

More particularly, the invention provides an orthopedic splint comprising a generally rigid splint core having one to a plurality of fabric layers impregnated with a hardened resin, the splint core having a predetermined circumferential width and a predetermined length and having inner and outer faces, a web-like securement member capable of at least partially encircling the splint for securing the splint to the body part being treated and having flexible hooks on the surface of the member which faces the body part, and inner and outer cover sheets of nonwoven fibrous fabric which substantially completely cover the inner and outer faces of the splint core and which include loops that are engageable by the flexible hooks of the securement device. Thus, the securement member may be engaged with the splint in a variety of positions, making removal and replacement of the splint relatively easy.

In accordance with a preferred embodiment of the invention, the cover sheets comprise nonwoven sheets of staple fibers. The fibers preferably are polyester fibers which are formed into cover sheets having a thickness of about 1/64-inch to 1/4-inch and a basis weight of about 3 to 12 ounces per square yard. The sheets preferably are constructed of polyester fibers of about 2–4 denier which are greater than about 2 inches in length.

Advantageously, the securement member is releasably engageable with the outer cover sheet such that at least about 2.5 pounds per square inch of in-plane force is required to detach the securement member from the outer cover sheet. Accordingly, a firm releasable bond is established between the securement member and the outer cover sheet, reducing the likelihood of inadvertent detachment of the securement member. Thus, the invention allows improved fastening, which is particularly desirable in veterinary applications.

In accordance with another preferred embodiment the invention provides a splinting assembly which permits substantial freedom in modifying the size and/or shape of a splint to the particular body part being treated, unhindered by any requirement to preserve the integrity of stitching or other fastening means between the various components of the splint. More specifically, the invention provides a splinting assembly which includes a hardenable splint core formed as a flexible sheet-like structure having a predetermined width and a predetermined length and having opposite faces, the splint core comprising one to a plurality of fabric layers and being impregnated with a water-curable and hardenable resin which is activated upon exposure to water and has a predetermined set time during which the resin remains sufficiently pliable to permit manipulation of the splint core to conform to the body part. The splint assembly further includes a first cover sheet having a predetermined length and width for substantially completely covering one of the faces of the splint core, and a second cover sheet having a predetermined length and width for substantially completely covering the other face of the splint core. Each of the cover sheets is formed of staple fibers held together to form a nonwoven fibrous fabric having substantial coherence such that individual fibers cannot readily be pulled out of the sheet. The cover sheets have sufficient porosity to permit uncured resin to penetrate into the surfaces of the sheets such that the sheets are bonded to the splint core upon hardening of the resin. However, the sheets have sufficient basis weight and thickness to prevent uncured resin from penetrating entirely through the sheets to their outer surfaces during the predetermined set time of the splint core. Additionally, and in accordance with a further preferred aspect of the invention, the cover sheets also serve as insulation preventing exposure of the body part to excessive temperature from the exothermic reaction of the resin.

In accordance with a method aspect of the invention, the invention provides a method of forming an orthopedic splint for a non-human animal body part, comprising the steps of providing a hardenable splint core formed as a flexible sheet-like structure having opposite faces and having a predetermined length and a predetermined width, the splint core comprising one to a plurality of fabric layers and being impregnated with a water-curable and hardenable resin which is activated upon exposure to water and has a generally predetermined set time during which the resin remains sufficiently pliable to permit manipulation of the splint core to conform to the body part. The method further includes providing a pair of cover sheets of nonwoven fibrous fabric each having a predetermined length and width not less than the length and width of the splint core, each cover sheet having sufficient porosity to permit uncured resin to penetrate into the surface of the sheet such that the sheet is bonded to the splint core upon hardening of the resin, and each cover sheet having sufficient basis weight and thickness to prevent uncured resin from penetrating entirely through the sheet to an outer surface thereof during the predetermined set time of the splint core. The splint core is soaked with water to activate the water-curable resin and is placed atop one of the cover sheets, and the other cover sheet is placed atop the soaked splint core such that the cover sheets substantially completely cover the opposite faces of the splint core, so as to form a flexible and shapable splint assembly. Next, the splint assembly is manipulated to cover and substantially conform to the shape of the body part, and the resin is allowed to cure and harden so as to form a generally rigid splint which substantially conforms to the shape of the body part and which has the cover sheets adhered to the splint core by contact with the resin to form a unitary splint.

The method of the invention facilitates tailoring the size and/or shape of the splinting assembly to the particular body part being treated. Thus, prior to allowing the resin to cure and harden, the practitioner can, if desired, cut off an end portion of the splint core so as to adapt the length thereof to that of the body part to be splinted, and additionally or alternatively, can cut off a longitudinally extending edge portion of the splint core so as to adapt the width thereof to the body part to be splinted.

In some cases, a practitioner may wish to immobilize a joint between a limb and foot. Accordingly, the invention also provides an orthopedic splint for an animal appendage and foot, comprising an appendage encircling portion configured as a trough-shaped structure for partially encircling the appendage and extending along at least a portion of the length of the appendage, and a foot-supporting platform integrally formed with the appendage-encircling portion and having a generally flat bottom portion for supporting the foot thereon. The bottom portion of the foot-supporting platform has a transverse width which exceeds the circumferential width of the appendage-encircling portion. Thus, the splint is suitable for use on an animal having a foot which is substantially wider than the limb to which it is joined, for example a dog.

The invention also provides a kit for forming a splint, which is suitable for use both in an office environment as well as in a remote field location. The kit includes a hardenable splint core formed as a flexible sheet-like structure having opposite faces, the splint core comprising one to a plurality of fabric layers and being impregnated with a water-curable and hardenable resin and being precut to have a plan shape with a predetermined length and a predetermined width. The kit further includes a pair of cover sheets each having a predetermined length and a predetermined width at least as great as the length and width of the splint core such that the cover sheets are capable of completely covering the opposite faces of the splint core, and a cutting implement capable of cutting the splint core and the cover sheets for adapting the size or shape of the splint core and cover sheets to a particular animal body part.

The kit preferably also includes stretchable polyolefin bandaging material which has an antimicrobial agent applied thereto, for pre-wrapping a wound dressing or fracture site prior to splinting, as well as cotton padding material which is also treated with antimicrobial agent, for wrapping over the polyolefin bandaging before splinting.

BRIEF DESCRIPTION OF THE DRAWINGS

The above and other objects, features, and advantages of the invention will become more apparent from the following description of certain preferred embodiments thereof, when taken in conjunction with the accompanying drawings, in which:

FIG. 1 is a perspective view of a splint with an integral foot support in accordance with the invention, showing the splint being worn by an animal;

FIG. 2 is a cross-sectional view taken on line 2—2 of FIG. 1, showing the multilayered construction of the splint;

FIG. 3 is a perspective view illustrating the method of shaping the flexible splint assembly of the present invention to form a splint similar to that shown in FIG. 1;

FIG. 4 is a perspective view of a sealed package containing a flexible resin-impregnated splint core in accordance with the invention;

FIG. 9 is a perspective view of another splint formed in accordance with the invention;

FIG. 10 is a perspective view of still another splint of the invention, shown in use on the leg of a horse;

FIG. 11 is a perspective view illustrating the method of shaping a flexible splinting assembly of the invention to form the splint of FIG. 10.

DETAILED DESCRIPTION OF THE DRAWINGS

Figure 5:
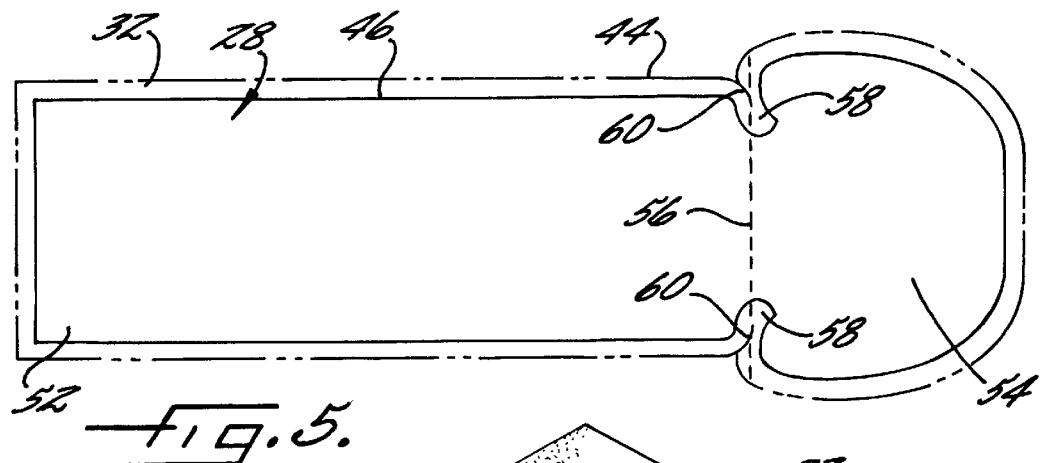
FIG. 5 is a schematic top plan view of a splint core and outer fabric cover which are die-cut to a shape suitable for forming a splint with integral foot support such as shown in FIG. 1.

The invention is now explained by reference to certain preferred embodiments thereof. It will be understood, however, that the invention is not limited to the embodiments shown and described herein.

With reference to FIG. 1, a splint 20 in accordance with the invention is depicted in use on a lower limb L and foot F of a small animal A. The splint 20 comprises a unitary structure including an appendage portion 22 and a foot-supporting platform 24 which is formed integrally therewith. The splint 20 is held in place on the animal's leg and foot by straps 26.

FIG. 2 depicts a cross-sectional view of the splint 20. The splint 20 is formed of a splint core 28 comprising a plurality of layers 30 of a knit fabric impregnated with a water-curable resin, and a pair of outer fabric covers 32 which cover opposite faces of the splint core 28. As shown in FIG. 2 and also visible in FIG. 1, the limb L of the animal is typically wrapped with one or more layers of a bandaging material 34 before the splint 20 is applied to the limb. Additionally, one or more layers of a padding material 36 are advantageously wrapped over the bandaging material 34 before the splint 20 is applied to the limb. As further described below, the outer fabric covers 32 are releasably engageable by the straps 26 which have a plurality of flexible hooks 38 that grasp loops 40 formed on the surface of the outer fabric cover 32.

The splint core 28 preferably comprises layers 30 of a knit, open-mesh fabric impregnated with a water-curable and hardenable resin. Various types of fibers may be used for forming the fabric layers 30, including fiberglass, polyester, polyolefin, and others. Preferably, the fabric layers comprise heat-cleaned fiberglass yarn knit into an open-mesh fabric. The fabric can be knit on various and numerous knitting apparatus. However, it is preferred that Raschel Warp Knitting apparatus be employed. Preferably, the knitting machine should include 6 to 28 needles per inch and more preferably, should include between 10 and 18 needles per inch. A particularly advantageous Raschel-knit fabric for use in the present invention has a basis weight of about 30–40 grams per square yard and a thickness of about 0.015–0.025 inch as measured on a Starrett Model 1010 machine using a ¼-inch presser foot, and an extensibility of about 20 percent, with about 18 wales per inch and about 14 courses per inch. However, various designs of the knit fabric may be employed depending upon the particular requirements of a given application.

Following construction of the fabric, the desired number of layers 30 of the fabric are assembled to form a splint core, and the splint core is coated with a hardenable liquid resin capable of curing to form a hardened plastic. Preferably, the hardenable liquid resin is a polyurethane prepolymer which is applied in a dry atmosphere to the splint core by injecting a preset amount of the resin through a slot die onto an upper surface of the splint core. The coated splint core is then immediately packaged in a sealed pouch which is purged with an inert gas such as nitrogen, so as to prevent moisture from contacting the splint core until it is to be used. The weight of the prepolymer is typically within the range of between about 60 and about 400 grams per square meter, preferably between about 80 and 300 grams per square meter to thereby provide a prepolymer weight between about 30% and 70% by weight, based on the weight of precoated fabric. The prepolymer generally contains polyisocyanates, polyols, a catalyst, and antifoaming and/or other ingredients. Preferred water curable polyurethane prepolymers for use in this invention are disclosed in Yoon, U.S. Pat. No. 4,433,680, which is hereby incorporated herein by reference. A preferred catalyst is Texacatt DMDEE catalyst available from Texaco.

For a small animal such as a dog or domestic house cat, a splint core 28 formed of three layers 30 of resin-impregnated Raschel-knit fiberglass fabric has been found to be suitable for achieving adequate strength and rigidity of a splint 20. Where increased strength and rigidity are needed, such as for larger animals, a greater number of layers 30 may be employed, as further described below.

Figure 6:
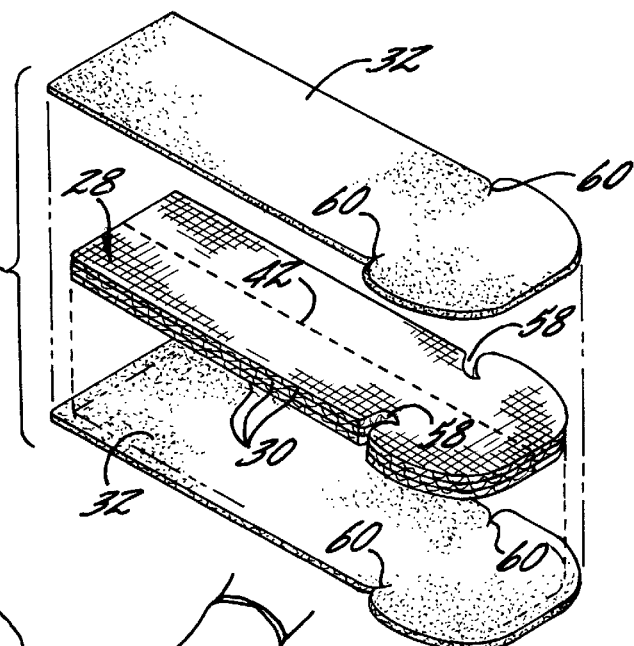
FIG. 6 is an exploded perspective view of a splinting assembly in accordance with the invention, showing the splint core disposed between outer fabric covers which extend slightly beyond the edges of the splint core.

FIGS. 5 and 6 depict the construction and method of making a splint such as the splint 20 of FIG. 1. As previously described, the splint core 28 comprises three layers 30 of resin-impregnated knit fabric. The three layers 30 are fastened together by a thread 42 stitched through the layers 30 down the longitudinal center lines thereof. The splint core 28 is a die-cut article, i.e., it is pre-cut to a plan shape suitable for forming a splint with an integral foot support such as the splint 20 of FIG. 1. The splint core 28 may be die-cut on a die cutting press, such as a press commonly known as a "clicker" press of the type well-known to those in the cut and sew industry. Similarly, the fabric covers 32 are preferably die-cut with a plan shape similar to that of the splint core 28. As shown, the fabric covers 32 are formed slightly larger in plan area so that the peripheral edges 44 of the covers 32 extend slightly beyond the peripheral edges 46 of the splint core 28.

As shown in FIG. 4, the pre-cut splint core 28 is contained in a sealed flexible foil pouch or package 48 until just prior to use. The pouch 48 prevents moisture from contacting the resin in the splint core 28, so that the splint core 28 remains flexible.

To form a splint with an integral foot support in accordance with the invention, the splint core 28 is removed from the foil pouch 48 and is briefly immersed in water. It is sufficient to fully submerge the splint core 28 for about two to three seconds. The splint core 28 is then removed from the water. If desired, excess water may be blotted from the splint core 28 with absorbent blotting paper or the like. The wet splint core 28 is then laid atop one of the fabric covers 32, and the other fabric cover 32 is then laid atop the splint core 28, as shown in FIG. 6, to form a splinting assembly 50. It will be noted that the splinting assembly 50 comprises two portions, an appendage-encircling portion 52 and a foot portion 54. The appendage-encircling portion 52 has a transverse width selected so as to wrap only partially about the circumference of the limb L, preferably about halfway around the limb, and has a longitudinal length selected in accordance with the length of the limb L or portion thereof to be splinted. Because the foot of a small animal is typically wide in relation to the limb, the foot portion 54 advantageously has a transverse width greater than that of the appendage-encircling portion 52, and a longitudinal length selected in accordance with the length of a typical small animal's foot. The appendage-encircling portion 52 and foot portion 54 are connected along an imaginary fold line 56 about which the foot portion 54 will be rotated relative to the appendage-encircling portion 52.

To facilitate folding the splint core 28 along the fold line 56, the splint core 28 includes a pair of notches 58 which extend from each of the longitudinal edges of the splint core 28 generally inwardly along the fold line 56. The notches 58 permit the foot portion 54 to be rotated along the fold line 56 relative to the appendage-encircling portion 52 without substantial bunching of the splint core 28 at the fold line 56. The fabric covers 32 preferably also have slits 60 which extend inwardly generally along the fold line 56.

Thus, once the splint core 28 has been soaked in water and the fabric covers 32 and splint core 28 have been assembled into the splinting assembly 50, the practitioner applies the splinting assembly 50 to the limb and foot of the animal as shown in FIG. 3. The appendage-encircling portion 52 of the splinting assembly 50 is wrapped about the limb L so as to partially encircle the limb, and such that the fold line 56 defined by the notches 58 is approximately coincident with the joint between the limb L and the foot. The foot portion 54 is rotated about the fold line 56 and shaped to the foot to form a foot-supporting platform 62. The foot-supporting platform 62 includes a generally flat bottom portion 64, and may also include opposite sidewalls 66 which upstand from opposite side edges of the bottom portion 64. Thus, it will be appreciated that the splinting assembly 50 is bent along two different directions at the fold line 56 in forming the foot supporting platform 62. The notches 58 allow this folding in two directions so that there is only a minimal amount of overlap of the splint core 28 at the edges where the sidewalls 66 join with the lower end of the appendage-encircling portion 52 of the splint. By minimizing the amount of overlap and bunching of the splint core 28, the invention facilitates the construction of a splint in which the inner surface which is against the animal's limb and foot is substantially smooth and free of bulges or protrusions which might lead to the formation of pressure ulcers or the like or which might cause discomfort to the animal.

Figure 7:
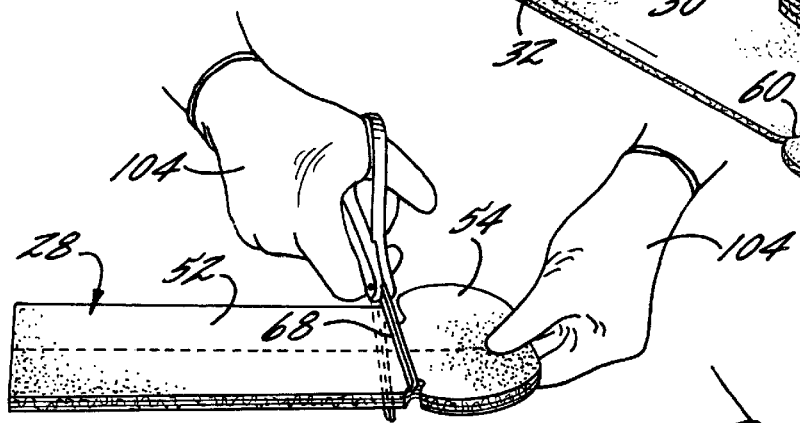
FIG. 7 is a perspective view illustrating the step of cutting off an end portion of a splint core to adapt the length of the core to a particular end use.
Figure 8:
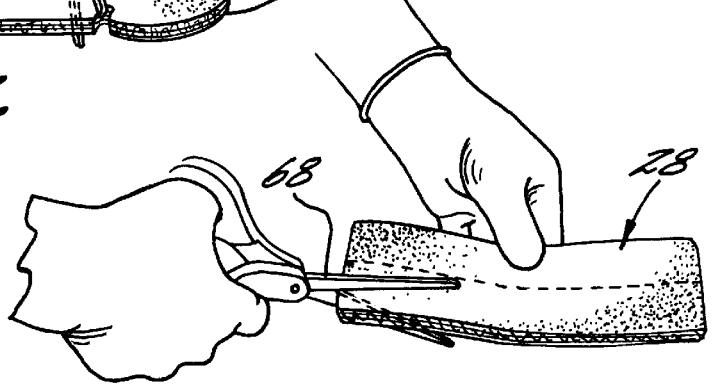
FIG. 8 is a perspective view illustrating the step of cutting off a longitudinally extending edge portion of a splint core to adapt the width of the core to a particular end use.

In some cases, a foot portion may not be desired or required. FIG. 7 illustrates that the foot portion 54 may be removed by cutting the splint core 28 along a transverse line. The fabric covers 32 may similarly be modified, and a splinting assembly fabricated from the shortened splint core and fabric covers for application to the limb only. Additionally, should the width of the splint core 28 exceed that required for partially encircling a limb, the splint core 28 may be cut as shown in FIG. 8 to remove a longitudinally extending edge portion so as to adapt the width of the splint core to the size of the limb to be splinted. Any suitable cutting implement, such as scissors 68, may be used for modifying the size and/or shape of the splint core 28 and covers 32.

A splinting assembly of the present invention can also be adapted to a curved or otherwise non-straight shape, such as for extending along a bent joint area of an animal appendage. As illustrated in FIG. 9, a splinting assembly 70 is shown being shaped to conform to a curved portion of an animal limb or appendage. The assembly 70 includes transversely extending slits 72 which are formed in the splint core 28 such as by scissors, to facilitate the bending of the assembly 70.

Once the splinting assembly has been manipulated and formed to partially encircle and conform to the animal limb or other body part to be splinted, the splinting assembly is held in shape and position for a sufficient time to allow the water-curable resin to harden. The amount of time from initial soaking of the splint core in water during which the resin remains sufficiently fluid to permit bending and shaping of the splint core typically is about two to five minutes, and the resin fully hardens within about five to ten minutes.

The fabric covers 32 advantageously comprise a fabric which is soft and thick so as to insulate the animal against the temperature created by the exothermic reaction of the curing resin, and which also has sufficient basis weight to prevent the resin from bleeding through the covers to the outer surface thereof. Additionally, the covers 32 advantageously are engageable by the securement members 26 for holding the splint in position on a body part. In accordance with a preferred embodiment of the invention, the covers 32 comprise a fabric formed of staple fibers which are processed to form a coherent sheet having a plurality of loops 40 at the outer surfaces of the sheet. The sheet preferably has a basis weight of about 3 to 12 ounces per square yard, and more preferably about 6 ounces per square yard. The sheet has a thickness which is preferably about 1/64 of an inch to about 1/4 of an inch, and more preferably about 1/32 of an inch. The staple fibers preferably are polyester, although other fiber types may be used.

Various methods may be used for forming the fibrous nonwoven fabric. In a preferred embodiment, the fibers of the sheet are highly entangled so that the sheet has a substantial coherency, i.e., individual fibers cannot readily be pulled from the sheet. In accordance with a preferred aspect of the invention, this is accomplished by needle-punching the sheet with approximately 1,800 penetrations per square inch, and by passing the sheet through the nip of heated rollers which compress and heat the sheet, so as to form a felt-like fabric. However, other methods of making a substantially coherent sheet of the preferred thickness and basis weight may be used.

The substantial coherency of the cover sheet accomplishes two advantages. First, the sheet bonds to the resin-impregnated splint core 28 by contact with the resin, and the cover 32 cannot readily be pulled off the splint core 28. Thus, no additional adhesive or stitching is required to secure the covers and the splint core together in a unitary splint. The second advantage of the coherency of the cover sheet is that the securement straps 26 can be engaged with the cover 32 at any portion thereof, and a substantial force must be exerted on the straps 26 to disengage them from the cover 32.

With reference again to FIG. 2, the securement member 26 comprises a strap or other web-like member having an inwardly-facing surface from which a plurality of flexible hooks 38 project. For example, the hooks 38 may comprise the hook member of a hook and loop fastener system, such as that marketed under the trademark VELCRO®. The hooks 38 readily grasp the loops 40 formed by the fibers at the surface of the cover sheet 32, so that more than a minimal amount of force is required to peel the securement member 26 from the cover 32. Accordingly, even if the splint core 28 and the cover sheets 32 are trimmed to adapt the width and/or the length of the splint to the body part to be splinted, the securement members 26 can always be secured to the splint to hold it in place on the body part. By thus eliminating the need for any dedicated fastener members on the splint, such as patches of loop material or the like, the invention permits substantial freedom in modifying the size and shape of a splint to a particular application.

To quantify the strength of the releasable bond between the fabric cover 32 and the securement strap 26, a tensile test was performed on a Chattilon tensile test machine. A relatively inextensible strap of VELCRO® hook material having about 300 nylon hooks per square inch (about 16 rows per inch with about 19 hooks per inch in each row) was prepared having a width of 1 inch and a length of several inches. A sheet of nonwoven needle-punched polyester was prepared having a thickness of 1/32-inch, and a basis weight of about 6 ounces per square yard, with about 1800 penetrations per square inch needle punching. The strap was engaged with the nonwoven sheet by firmly pressing the hooks against the sheet, so that the strap and the sheet overlapped for a length of about 1.5 inches. The strap was affixed between the fluted rollers of one of the movable members of the test machine, and the sheet was affixed between the fluted rollers of the other movable member of the machine. The machine was operated to pull the sheet and the strap in opposite directions in the common plane of the sheet and strap, and a load cell was used to measure the amount of in-plane force required to detach the strap from the sheet. The test determined that about 6 pounds of inplane force were required to cause detachment of the 1.5-inch by 1 inch engaged portion of the strap from the sheet, which translates into about 4 pounds of in-plane force per square inch. This strength is considered more than adequate. An acceptable strength for the releasable bond between the hook material and fabric cover of the invention is at least about 2.5 pounds of in-plane force per square inch.

In addition to the substantial engagement strength made possible by the nonwoven fabric covers of the invention, another benefit of the fabric is that its substantial coherency resists the tendency of individual fibers to be pulled from the fabric by the flexible hooks of the securement straps. With other types of fabrics, the flexible hooks of the straps can become clogged by fibers as the straps are repeatedly attached to and detached from the fabric. In contrast, the nonwoven fabric of the invention remains substantially intact, and the securement straps remain substantially free of fibers even with repeated attachment and detachment of the straps.

While the splints described thus far have focused primarily upon small animals, the invention is not limited in this respect, and also encompasses splints for larger body parts and larger animals. For example, FIGS. 10 and 11 depict a splint in accordance with the invention for splinting a limb L of a large animal such as a horse. With reference first to FIG. 11, a splinting assembly 80 is shown which comprises a splint core 82 formed of a plurality of layers 84 of a resin-impregnated fabric as previously described, and a pair of outer covers 86 which substantially completely cover the opposite faces of the splint core 82. For a larger animal, the splint core 82 preferably comprises about 7 to 10 layers of resin-impregnated knit fiberglass fabric. As with the previous embodiments, the splint core 82 is soaked with water and is sandwiched between the cover sheets 86 to form the splinting assembly 80, and the assembly 80 is then applied to the limb L to be splinted. Preferably, a bandaging material 88 is wrapped around the limb L prior to splinting, and a layer of padding material 90 is applied over the bandage 88 prior to splinting. The splinting assembly 80 is manipulated to partially encircle and conform to the limb L, and is held in position and shape until the resin hardens.

The splint 80 is secured to the limb L by one or more web-like securement members 92. Each securement member 92 comprises a web-like member capable of completely encircling the splint 80 and limb L at least once. At the two opposite ends of the securement member 92, the inwardly facing surface 94 which faces the splint 80 and limb L has a plurality of flexible hooks 96 projecting therefrom. Between the two end portions having the hooks 96, the outwardly facing surface of the securement member 92 has a loop material 98 affixed thereto and positioned for engagement by the free end having the hooks 96. Thus, a first end of the securement member 92 is engaged with the outer cover 86 of the splint 80, and the securement member 92 is wound about the splint and limb, and then the free end of the securement member is affixed either to the outer cover 86 or to the loop material 98.

Figure 12:
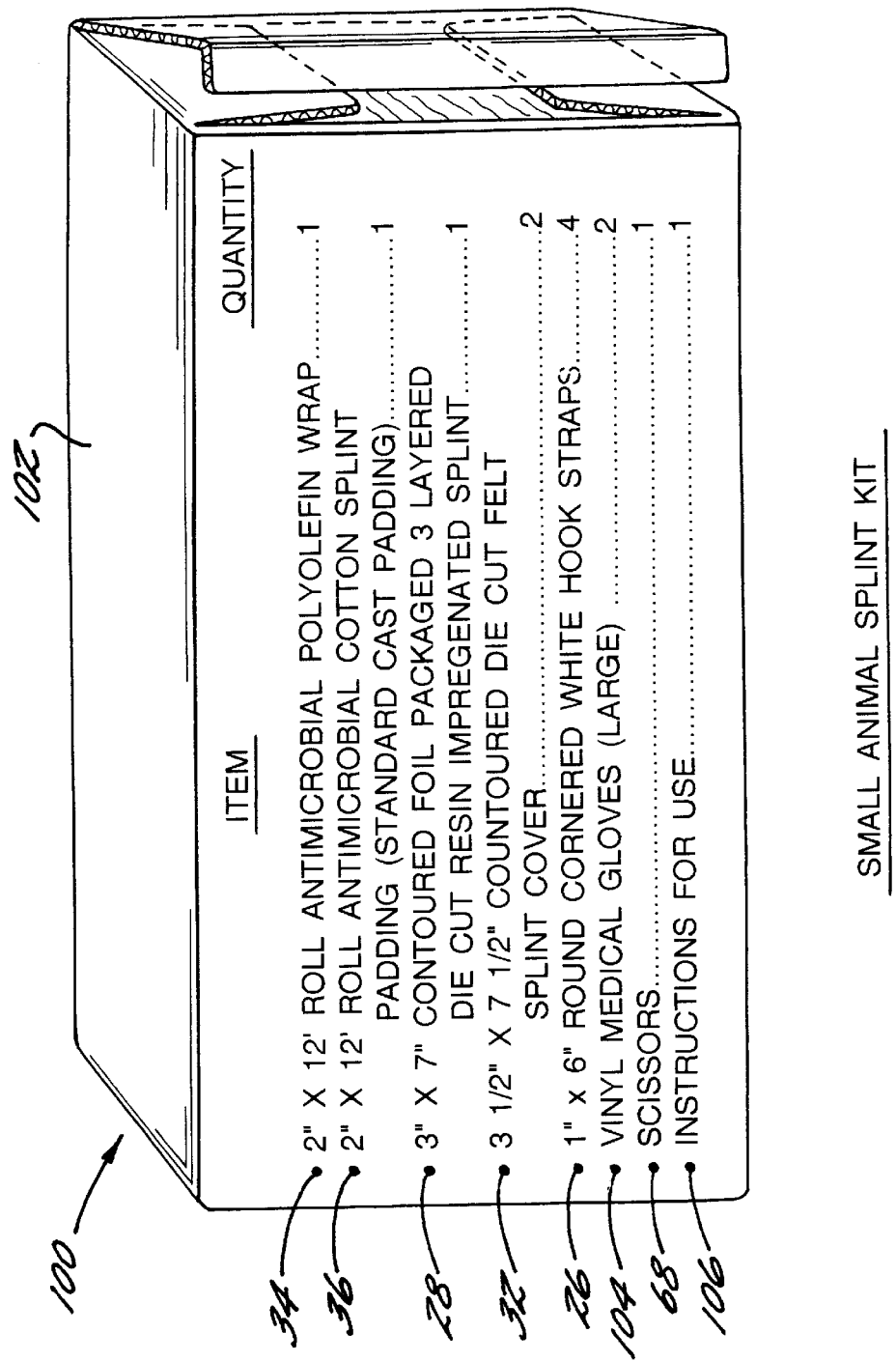
FIG. 12 is a diagrammatic depiction of a kit of materials for making a splint for a small animal in accordance with the invention.

The invention also provides a kit which contains the materials necessary for creating a splint either in a practitioner's office or in a remote field location. FIG. 12 diagrammatically depicts a kit in accordance with a preferred embodiment of the invention. The kit 100 of FIG. 12 is suitable for making a splint for a small animal such as a dog or domestic house cat. The kit 100 includes a carton 102 containing a roll of extensible polyolefin fabric 34 (see also FIG. 2) which preferably is treated with an antimicrobial agent to inhibit growth of bacteria; a roll of cotton splint padding 36 (see also FIGS. 1 and 2) which likewise is treated with an antimicrobial agent; a die-cut resin-impregnated splint core 28 contained in a sealed foil package; a pair of die-cut fabric splint covers 32 sized slightly larger than the splint core 28; at least one and preferably a plurality of securement straps 26 which have flexible hooks for attachment to the fabric splint covers; a pair of vinyl or other resin-impervious gloves 104; a pair of scissors 68 or other cutting implement for trimming the splint core and fabric covers; and instructions 106 for using the splint kit 100.

The antimocrobial polyolefin wrap 34 is suitably a bandaging material marketed under the trademark WONDR-WRAP and available from K. R. Ferguson Technologies, Inc. of Charlotte, N.C. The antimicrobial splint padding 36 is suitably a cotton padding material marketed under the trademark DRI-GUARD and also available from K. R. Ferguson Technologies, Inc.

In use, the practitioner dons the protective gloves 104, and applies the antimicrobial polyolefin wrap 34 over the wound dressing or fracture site, preferably overlapping the turns of the wrap to achieve a double thickness. The polyolefin wrap 34 should extend over the entire length of the portion of the limb which will be covered by the splint. Next, the practitioner wraps the antimicrobial cotton splint padding 36 over the polyolefin wrap 34 with several thicknesses at the top and bottom of the splint. The practitioner then uses the scissors 68 to cut the fabric splint covers 32, if any cutting is needed to adapt the splint to the body part being treated, and the splint core 28 is removed from the foil package and also trimmed (see FIGS. 7 and 8), if necessary, to adapt the splint core to the body part. The scissors 68 advantageously are disposable so that they need not be cleaned to remove resin from them, but can simply be discarded after the splint is completed.

After any trimming which may be required, the practitioner immerses the splint core 28 in water for two to three seconds, and then removes the splint core and blots excess water therefrom. The splint core is centered over one of the fabric splint covers 32. The practitioner then removes the gloves 104 and positions the other fabric cover 32 over the splint core to form the splint assembly 50 as shown in FIG. 6. The splint assembly is then applied and conformed to the body part as previously described. The securement members 26 are used to secure the splint in place on the body part.

During the manipulation of the splint assembly to conform to the body part, some of the resin from the splint core 28 penetrates partially into the surface of the adjacent fabric covers 32. Accordingly, upon hardening of the resin, the covers are firmly bonded to the splint core. However, the fabric covers 32 have sufficient thickness and basis weight to prevent the resin from penetrating entirely through the covers to their outer surfaces. Accordingly, the practitioner can manipulate the splint assembly with bare hands.

The invention also encompasses kits for animals other than small animals, including kits for large animals such as horses. As should be evident, the splint core and fabric covers are appropriately sized for the larger body parts of a horse. For instance, a splint kit for splinting a leg of a horse includes a splint core formed of ten layers of fiberglass knit fabric impregnated with water-curable resin and having dimensions of about 5 inches by 14 inches. The fabric covers advantageously have dimensions of about 7 inches by 16 inches. The large animal kit also includes securement members such as the securement members 92 shown in FIG. 10, having hooks on the inwardly facing surface at the ends of the securement member, and loop material on the outwardly facing surface between the ends. The polyolefin wrap and cotton splint padding advantageously are supplied in four-inch-wide rolls rather than the two-inch-wide rolls used with the small animal kit.

The description thus far has assumed that two separate nonwoven fabric covers 32, 86 are employed for covering the outer faces of the splint core 28, 82. However, it will be appreciated that a single sheet of nonwoven fabric may alternatively be employed by folding the sheet to form two opposing portions for covering the opposite faces of the splint core. Accordingly, the term "cover sheet" as used throughout the specification and appended claims is intended to encompass both a discrete cover sheet separate from another cover sheet used in the same splint, as well as a portion of a single sheet which serves as a cover sheet for one face of a splint core, with another portion of the sheet serving as the other cover sheet.

While the invention has been explained by describing certain preferred embodiments thereof, and while these embodiments have been described in considerable detail, it is to be understood that the invention is not limited to the embodiments which have been illustrated and described. Various modifications and substitutions of equivalents may be accomplished within the scope of the invention. Accordingly, the scope of the invention is to be determined by reference to the appended claims.

What is claimed is:

1. An orthopedic splint for a body part of an animal, comprising:

a generally rigid splint core having one to a plurality of fabric layers impregnated with a hardened resin, the splint core having a predetermined circumferential width and a predetermined length and having inner and outer faces;

a web-like securement member capable of at least partially encircling the splint for securing the splint to the body part, the member having flexible hooks on the surface of the member which faces the body part; and an inner cover sheet substantially completely covering the inner face of the splint core, and an outer cover sheet substantially completely covering the outer face of the splint core;

each of the cover sheets being formed of a nonwoven fibrous fabric which has a plurality of loops on the surfaces thereof for removably engaging the flexible hooks of the securement member to fix the securement member in a position at least partially encircling the splint, the securement member being engageable with any portion of the surface of the outer cover sheet to facilitate wrapping and fixing the securement member about the body part and splint in various positions.

2. The splint of claim 1, wherein each cover sheet is adhered to the splint core by disposing the cover sheet against the corresponding face of the splint core prior to the resin hardening so that resin penetrates into the surface of the cover sheet, and then allowing the resin to harden.

3. The splint of claim 2, wherein the splint core comprises one to a plurality of layers of glass fiber knit fabric impregnated with a polyurethane resin.

4. The splint of claim 3, wherein each cover sheet comprises staple fibers formed into a sheet having a thickness of about 1/64-inch to about 1/4-inch and a basis weight of about 3–12 ounces per square yard.

5. The splint of claim 4, wherein the staple fibers comprise polyester fibers which are about 2–4 denier and are at least about 2 inches in length.

6. The splint of claim 5, wherein the flexible hooks of the securement member comprise nylon hooks.

7. The splint of claim 1, wherein the securement member is releasably engageable with the outer cover sheet such that at least about 2.5 pounds per square inch of in-plane force is required to detach the securement member from the outer cover sheet.

8. An orthopedic splinting assembly adapted to be applied in a flexible state to a body part of an animal and thereafter hardened so as to form a splint for the body part, and comprising:

a hardenable splint core formed as a flexible sheet-like structure having a predetermined width and a predetermined length and having opposite faces, the splint core comprising one to a plurality of fabric layers and being impregnated with a water-curable and hardenable resin which is activated upon exposure to water and has a generally predetermined set time during which the resin remains sufficiently pliable to permit manipulation of the splint core to conform to the body part;

a first cover sheet having a predetermined length and width for substantially completely covering one of the faces of the splint core; and a second cover sheet having a predetermined length and width for substantially completely covering the other face of the splint core;

each of the cover sheets comprising a sheet of nonwoven fibrous fabric having substantial coherence such that individual fibers cannot readily be pulled out of the sheet, the sheet having sufficient porosity to permit uncured resin to penetrate into the surface of the sheet such that the sheet is bonded to the splint core upon hardening of the resin, the sheet having sufficient basis weight and thickness to prevent uncured resin from penetrating entirely through the sheet to an outer surface thereof during the predetermined set time of the splint core.

9. The splinting assembly of claim 8, wherein the splint core comprises one to a plurality of layers of glass fiber knit fabric.

10. The splinting assembly of claim 9, wherein each cover sheet comprises staple fibers held together to form a sheet having a thickness of about 1/64-inch to about 1/4-inch and a basis weight of about 3–12 ounces per square yard.

11. The splinting assembly of claim 8, wherein each cover sheet has a thickness of about 1/32-inch and a basis weight of about 6 ounces per square yard.

12. A method of forming an orthopedic splint for a non-human animal body part, comprising the steps of:

providing a hardenable splint core formed as a flexible sheet-like structure having opposite faces and having a predetermined length and a predetermined width, the splint core comprising one to a plurality of fabric layers and being impregnated with a water-curable and hardenable resin which is activated upon exposure to water and has a predetermined set time during which the resin remains sufficiently pliable to permit manipulation of the splint core to conform to the body part;

providing a pair of cover sheets of nonwoven fibrous fabric each having a predetermined length and width not less than the length and width of the splint core, each cover sheet having sufficient porosity to permit uncured resin to penetrate into the surface of the sheet such that the sheet is bonded to the splint core upon hardening of the resin, and each cover sheet having sufficient basis weight and thickness to prevent uncured resin from penetrating entirely through the sheet to an outer surface thereof during the predetermined set time of the splint core;

soaking the splint core with water to activate the water-curable resin;

placing the soaked splint core atop one of the cover sheets and then placing the other cover sheet atop the soaked splint core such that the cover sheets substantially completely cover the opposite faces of the splint core, so as to form a flexible and shapable splint assembly;

manipulating the splint assembly to cover and substantially conform to the shape of the body part; and allowing the resin to cure and harden so as to form a generally rigid splint which substantially conforms to the shape of the body part and which has the cover sheets adhered to the splint core by contact with the resin to form a unitary splint.

13. The method of claim 12, further comprising the step, prior to allowing the resin to cure and harden, of cutting off an end portion of the splint core so as to adapt the length thereof to that of the body part to be splinted.

14. The method of claim 12, further comprising the step, prior to allowing,the resin to cure and harden, of cutting off a longitudinally extending edge portion of the splint core so as to adapt the width thereof to the body part to be splinted.

15. The method of claim 12, further comprising the step, prior to allowing the resin to cure and harden, of forming one or more slits in the longitudinal edges of the splint core to facilitate bending the splint core around the body part without substantial bunching of the splint core.

16. The method of claim 12, further comprising the step of securing the splint to the body part by wrapping a web-like securement member at least partially about the body part and splint, the member having flexible hooks on the surface of the member which faces the splint, and engaging the flexible hooks with the outer cover sheet so as to fix the securement member in the wrapped position.

17. An orthopedic splint for an animal appendage and a foot adjoined thereto, comprising:
- an appendage-encircling portion configured as a trough-shaped structure for partially encircling the appendage and extending along at least a portion of the length of the appendage, the appendage-encircling portion having a circumferential width; and
- a foot-supporting platform integrally formed with the appendage-encircling portion and having a generally flat bottom portion for supporting the foot thereon, the bottom portion having a transverse width which exceeds the circumferential width of the appendage-encircling portion.

18. The splint of claim 17, wherein the splint comprises a generally rigid splint core formed of one to a plurality of layers of fabric impregnated with a hardened resin, the splint core having inner and outer faces, and further including inner and outer covers bonded to the opposite faces of the splint core by contact with the resin.

19. The splint of claim 18, wherein the covers comprise sheets of non-woven fabriced material formed of staple fibers, each sheet having a thickness of about $1/64$-inch to $1/4$-inch.

20. The splint of claim 19, wherein the surfaces of the covers have a plurality of loops formed by the staple fibers, and further comprising a web-like securement member for securing the splint to the appendage, the member having flexible hooks on a surface of the member which faces the splint, the hooks being cooperable with the loops on the surfaces of the covers for releasably securing the securement member to the covers, such that the securement member can be wrapped at least partially about the appendage and splint and secured to the outer one of the covers to secure the splint to the appendage.

21. A splint core adapted to be applied in a flexible state to an animal appendage and a foot adjoined thereto and thereafter hardened so as to form an orthopedic splint for the appendage and foot, and comprising:
- a hardenable splint core formed as a flexible sheet-like structure having opposite faces, the splint core comprising one to a plurality of fabric layers and being impregnated with a water-curable and hardenable resin, the splint core having an elongated plan shape of predetermined length and having opposite longitudinal edges, each longitudinal edge of the splint core including a notch extending inwardly and generally toward the notch in the opposite longitudinal edge so as to define a fold line dividing the splint core into an appendage-encircling portion and a foot portion, the notches allowing the foot portion to be rotated about the fold line relative to the appendage-encircling portion without substantial bunching of the splint core at the longitudinal edges, such that the appendage-encircling portion can be wrapped to partially encircle the appendage, and the foot portion can be rotated about the fold line to form a generally flat platform for supporting the foot with no more than slight overlap of the splint core at the notches.

22. The splint core of claim 21, wherein the appendage-encircling portion has a predetermined width, and the foot portion of the splint core has a predetermined width greater than the width of the appendage-encircling portion such that a foot-supporting platform formed from the foot portion is capable of accommodating a foot which is wider than the appendage.

23. The splint core of claim 22, wherein the splint core is die cut to have a generally keyhole-shaped plan shape.

24. A splinting assembly adapted to be applied in a flexible state to an animal body part and thereafter hardened so as to form an orthopedic splint for the body part, and comprising:
- a hardenable splint core formed as a flexible sheet-like structure having a predetermined length and a predetermined width and having opposite faces, the splint core comprising a plurality of fabric layers and being impregnated with a water-curable and hardenable resin;
- a pair of cover sheets each having a predetermined length and a predetermined width selected such that the cover sheets are capable of substantially completely covering the opposite faces of the splint core, each of the cover sheets comprising a nonwoven fibrous fabric which has a plurality of loops on the surfaces thereof; and
- at least one strap for securing the assembly to the body part, the strap comprising an elongated flexible web of sufficient length to be wound more than a full turn about the appendage and having inwardly facing and outwardly facing surfaces, the opposite end portions of the strap having flexible hooks projecting from the inwardly facing surface thereof which are cooperable with the loops on the surfaces of the cover sheets for removably grasping the exposed surface of the outer cover sheet, and at least a portion of the outwardly facing surface of the strap between the end portions having a non-woven fibrous loop material removably graspable by the flexible hooks, such that the hooks at one end of the strap can be secured to the outer cover sheet and the strap wound about the body part and the splinting assembly, and the hooks at the other end of the strap can be secured to either the outer cover sheet or the loop material on the strap so as to secure the splinting assembly to the body part.

25. The splinting assembly of claim 24, wherein each cover sheet comprises staple fibers formed into a sheet having a thickness of about $1/64$-inch to about $1/4$-inch and a basis weight of about 3–12 ounces per square yard.

26. The splinting assembly of claim 24, wherein each cover sheet has a thickness of about $1/32$-inch and a basis weight of about 6 ounces per square yard.

27. The splinting assembly of claim 24, wherein the splint core comprises about 7 to 10 layers of glass fiber knit fabric impregnated with water-curable resin.

28. A kit for forming a splint for an animal body part, and comprising:
- a hardenable splint core formed as a flexible sheet-like structure having opposite faces, the splint core comprising one to a plurality of fabric layers and being impregnated with a water-curable and hardenable resin, the splint core being precut-to have a plan shape with a predetermined length and a predetermined width;
- a pair of cover sheets each having a predetermined length and a predetermined width at least as great as the length and width of the splint core such that the cover sheets are capable of completely covering the opposite faces of the splint core; and
- a cutting implement capable of cutting the splint core and the cover sheets for adapting the size or shape of the splint core and cover sheets to a particular animal body part.

29. The kit of claim 28, further comprising a web-like securement member for wrapping about the body part and engaging a splint to secure the splint to the body part, the surface of the securement member which faces the splint including flexible hooks projecting therefrom, the hooks being removably engageable with the cover sheets so as to fix the securement member in a wrapped position about the body part and splint.

30. The kit of claim 28, further including gloves which are substantially impervious to the resin for protecting a user of the kit from contact with the resin.

31. The kit of claim 28, further including a bandage formed of stretchable polyolefin fabric for pre-wrapping the body part prior to applying the splint thereto, the bandage having an antimicrobial agent applied thereto.

32. The kit of claim 31, further including a padding material for wrapping over the polyolefin bandage prior to applying the splint, the padding material having an antimicrobial agent applied thereto.

33. The kit of claim 28, wherein the splint core comprises one to a plurality of layers of glass fiber knit fabric impregnated with a polyurethane prepolymer resin.

34. The kit of claim 28, wherein each cover sheet comprises staple polyester fibers each having a diameter of about 2–4 denier and a length of at least about 2 inches, each cover sheet having a thickness of about $\frac{1}{64}$-inch to $\frac{1}{4}$-inch and a basis weight of about 3–12 ounces per square yard.

35. The kit of claim 34, wherein each of the cover sheets is formed by a process which includes needle-punching the sheet with about 1800 penetrations per square inch, and heating and compressing the sheet, so as to form a sheet having substantial coherency.

* * * * *